United States Patent [19]

Krapcho et al.

[11] 4,179,558

[45] Dec. 18, 1979

[54] NAPHTHALENONE DERIVATIVES AND ANALOGS

[75] Inventors: John Krapcho; Joseph Schwartz, both of Somerset, N.J.

[73] Assignee: E. R. Squibb & Sons, Inc., Princeton, N.J.

[21] Appl. No.: 873,644

[22] Filed: Jan. 30, 1978

[51] Int. Cl.² .................. C07D 295/00; A01N 9/22
[52] U.S. Cl. .................. 544/174; 260/326.5 C; 260/390; 260/501.18; 260/570 R; 260/570.7; 424/248.56; 424/267; 424/274; 424/316; 424/330; 546/205
[58] Field of Search .............. 260/570 R, 293.62, 386, 260/326.5 C, 501.18, 390; 424/330; 544/174; 546/205

[56] References Cited

U.S. PATENT DOCUMENTS

3,506,653   4/1970   Fried .......................... 260/570.7 X

*Primary Examiner*—Robert V. Hines
*Attorney, Agent, or Firm*—Lawrence S. Levinson; Donald J. Barrack

[57] ABSTRACT

Compounds having the formula

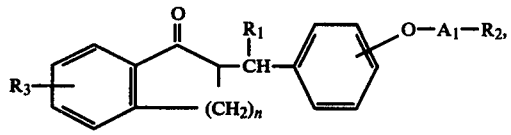

wherein $R_1$ is hydrogen, alkyl or aryl; $R_2$ is alkylamino, dialkylamino, or a nitrogen containing heterocyclic group; $R_3$ is hydrogen, halogen, alkyl, alkoxy or trifluoromethyl; $A_1$ is an alkylene group; and n is 1, 2 or 3, have useful anti-inflammatory activity.

18 Claims, No Drawings

NAPHTHALENONE DERIVATIVES AND ANALOGS

BRIEF DESCRIPTION OF THE INVENTION

Compounds having the formula

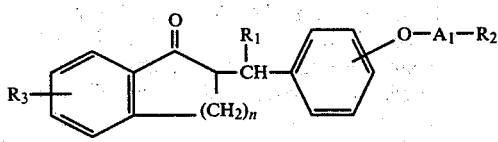

and the pharmaceutically acceptable salts thereof, have useful anti-inflammatory activity. In formula I, and throughout the specification, the variables are as defined below.

$R_1$ is hydrogen, alkyl, or aryl;

$R_2$ is alkylamino, dialkylamino, 1-piperidinyl, 1-pyrrolidinyl, 4-morpholinyl, 4-alkyl-1-piperidinyl or 4-(2-hydroxyethyl)-1-piperidinyl;

$R_3$ is hydrogen, halogen, alkyl, alkoxy or trifluoromethyl;

$A_1$ is a straight or branched chain alkylene group having 2 to 5 carbon atoms; and n is 1, 2 or 3.

The terms "alkyl" and "alkoxy" are used throughout the specification to refer to groups having 1 to 8 carbon atoms, preferably 1 to 4 carbon atoms.

The term "aryl" is used throughout the specification to refer to phenyl or phenyl substituted with a halogen, alkyl, alkoxy or trifluoromethyl group.

The term "halogen" is used throughout the specification to refer to fluorine, chlorine, bromine or iodine.

DETAILED DESCRIPTION OF THE INVENTION

The compounds of formula I, and the pharmaceutically acceptable salts thereof, can be prepared from the corresponding compound having the formula

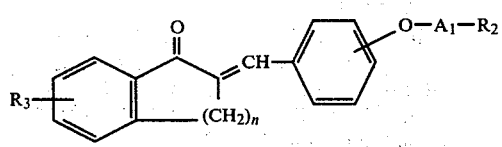

Compounds of formula II are known in the art; see, for example, the disclosure of U.S. Pat. No. 4,053,514, issued Oct. 11, 1977.

As disclosed in the prior art, the compounds of formula II are prepared by reacting a ketone having the formula

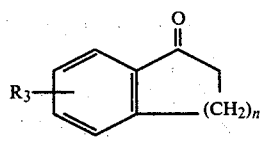

with a benzaldehyde derivative having the formula

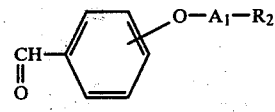

in an alkanol solvent at a reduced temperature of 0° C. to about −25° C. The reaction is preferably run in the presence of a base.

Those compounds of formula I wherein $R_1$ is alkyl or aryl are prepared by reacting the corresponding compound of formula II with the appropriate Grignard or lithium reagent having the formula $$R'_1-MgBr,$$  V or $$R'_1-Li.$$  VI The symbol $R'_1$ represents alkyl or aryl. When a Grignard reagent of formula V is used as a reactant the reaction is run at room temperature in an organic solvent, e.g., tetrahydrofuran. Optionally, the reaction may be run in the presence of trace amounts of metal halides. When a lithium reactant of formula VI is used, the reaction is run in an organic solvent, e.g., ether at the reflux temperature of the solvent.

Those compounds of formula I wherein $R_1$ is hydrogen are prepared by catalytic hydrogenation of the corresponding compound of formula II. Exemplary of the many art-recognized procedures of catalytic hydrogenation is the use of a palladium catalyst and an organic solvent (e.g., ethyl acetate) in a Parr hydrogenator.

The compounds of formula I form acid addition salts with inorganic and organic acids, using art-recognized procedures. Exemplary salts are the hydrohalides, sulfate, nitrate, phosphate, borate, acetate, pamoate, tartrate, citrate, maleate, benzoate, methanesulfonate, toluenesulfonate and the like.

The compounds of formula I, and the pharmaceutically acceptable salts thereof, are useful for the treatment of inflammation in mammalian species, e.g., rats, dogs, cats, monkeys, etc. Joint tenderness and stiffness (in conditions such as rheumatoid arthritis) are relieved by the above-described compounds.

The compounds of this invention, and the pharmaceutically acceptable salts thereof, can be formulated for use as antiinflammatory agents according to accepted pharmaceutical practice in oral dosage forms such as tablets, capsules, elixirs or powders, or in injectable form in a sterile aqueous vehicle prepared according to conventional pharmaceutical practice. The compounds of this invention may be administered in amounts of 100 milligrams per 70 kilograms of animal body weight per day to 2 grams per 70 kilograms of animal body weight per day, preferably 100 milligrams per 70 kilograms of animal body weight per day to 1 gram per 70 kilograms of animal body weight per day.

The following examples are specific embodiments of this invention.

EXAMPLE 1

2-[1-[4-[3-(Dimethylamino)propoxy]phenyl]ethyl]-3,4-dihydro-1(2H)-naphthalenone, oxalate salt (1:1)

(A)

2-[[4-[3-(Dimethylamino)propoxy]phenyl]methylene]-3,4-dihydro-1(2H)-naphthalenone A stirred solution of 50 g of α-tetralone and 70 g of 4-(3-dimethylaminopropoxy)benzaldehyde in 275 ml of ethanol is cooled to −20° C. and treated with 2.0 g of potassium hydroxide dissolved in 50 ml of ethanol. The cooling bath is removed and after standing for about 16 hours at room temperature the reaction mixture (some product has separated) is added to 1.2 liters of cold water. The material is extracted with 3:1 ether-dichloromethane (five 300 ml portions), the combined extracts are dried over magnesium sulfate, and the solvents are removed on a rotary evaporator to give a semi-solid residue. Crystallization of the residue from 300 ml of diisopropyl ether yields 86 g of product; melting point 86°–88° C.

(B)

2-[1-[4-[3-(Dimethylamino)propoxy]phenyl]ethyl]-3,4-dihydro-1(2H)-naphthalenone, oxalate salt (1:1)

A stirred solution of 15 g of 2-[[4-[3-(dimethylamino)propoxy]phenyl]methylene-3,4-dihydro-1(2H)-naphthalenone in 150 ml of tetrahydrofuran is treated with 25 ml of 3 M methyl magnesium bromide; the temperature rises to 50° C. After 4 hours at room temperature the mixture is poured into a cold solution of 7.0 g of ammonium chloride in 70 ml of water and the product is extracted with ether (three 150 ml portions). The combined extracts are dried over magnesium sulfate and the solvent removed on a rotary evaporator to give 16.7 g of the free base of the title compound as an oil.

The base (13.2 g) is dissolved in 65 ml of acetonitrile and treated with a warm solution of 3.4 g of oxalic acid in 50 ml of acetonitrile. On seeding, the crystalline oxalate salt rapidly separates. After cooling overnight, the product weighs 12.9 g and has a melting point of 100°–103° C. (sintering at 97° C.). Crystallization from 60 ml of acetonitrile gives 12.2 g of the title compound, melting point 101°–103° C. (sintering at 97° C.).

EXAMPLE 2

2-[1-[4-[3-(Dimethylamino)propoxy]phenyl]pentyl]-3,4-dihydro-1(2H)-naphthalenone, oxalate salt (1:1)

A stirred solution of 10 g of 2-[[4-[3-(dimethylamino)propoxy]phenyl]methylene]-3,4-dihydro-1(2H)-naphthalenone (prepared as described in Example 1A) in 160 ml of ether is treated in a steady stream with 22 ml of a 2.4 molar hexane solution of butyl lithium (cooled slightly to moderate refluxing). After the addition, the mixture is stirred at room temperature for 1 hour, refluxed for 1 hour, cooled, and poured with stirring into an ice-cold solution of 12 g of ammonium chloride in 60 ml of water. The layers are separated, the aqueous phase extracted with ether (three 100 ml portions), the combined ether layers are dried over magnesium sulfate and the solvent removed on a rotary evaporator to give 12.6 g of the free base of the title compound as a crude viscous oil.

The base (11.9 g) in 40 ml of acetone is treated with a solution of 2.8 g of oxalic acid in 20 ml of acetone to give the solid oxalate salt. After cooling for 2 days the salt weighs 9.7 g, melting point 92°–94° C. (sintering at 89° C.). Following crystallization from 100 ml of acetone-20 ml acetonitrile, the title compound weighs 6.5 g, melting point 96°–98° C. (sintering at 90° C.).

EXAMPLE 3

2-[[4-[3-(Dimethylamino)propoxy]phenyl]phenylmethyl]-3,4-dihydro-1(2H)-naphthalenone, hydrochloride (1:1)

A stirred solution of 15 g of 2-[[4-[3-(dimethylamino)propoxy]phenyl]methylene]-3,4-dihydro-1(2H)-naphthalenone (prepared as described in Example 1A) in 150 ml of tetrahydrofuran is treated with 25 ml of 3 molar ethereal phenyl magnesium bromide; the temperature rises to about 50° C. After stirring for 4 hours at room temperature, the solution is poured into an ice-cold solution of 7 g of ammonium chloride in 70 ml of water and the product is extracted with ether (three 150 ml portions). The combined extracts are dried over magnesium sulfate and the solvent removed on a rotary evaporator to give 21.2 g of the free base of the title compound as a viscous oil.

The base (19.7 g) is dissolved in 100 ml of ethanol, cooled, treated with 7.5 ml of 5.6 N alcoholic hydrogen chloride (90% of theory; excess hydrogen chloride causes dark coloration), and diluted to 450 ml (just short of cloudiness) with ether. On seeding and rubbing, the crystalline hydrochloride salt slowly separates; crude yield, after 1 week in the cold, 11.2 g, melting point 173°–175° C. Following crystallization from 25 ml of acetonitrile, the title compound weighs 7.1 g, melting point 175°–177° C.

EXAMPLE 4

2-[[4-[3-(Dimethylamino)propoxy]phenyl]methyl]-3,4-dihydro-1(2H)-naphthalenone, hydrochloride (1:1)

A mixture of 9.6 g of 2-[[4-[3-(dimethylamino)propoxy]phenyl]methylene]-3,4-dihydro-1(2H)-naphthalenone (prepared as described in Example 1A), 1 g of 5% palladium on carbon and 100 ml of ethyl acetate is shaken on the Parr hydrogenator for 3 hours. The mostly solid residue from the ethyl acetate evaporation is rubbed under 150 ml of hexane and cooled overnight to give 7.9 g of solid base, melting point 68°–70° C. (sintering at 57° C.). Crystallization from 20 ml of acetonitrile yields 6.4 g of the free base of the title compound, melting point 74–76° C.

A stirred solution of the base (6.3 g) in 300 ml of ether is treated with 100 ml of ether containing 3.5 ml of 5.5 N alcoholic hydrogen chloride to give the solid hydrochloride salt which weighs, after cooling for about 16 hours, 6.8 g, melting point 215°–217° C. (sintering at 210° C.). Following recrystallization from 70 ml warm methanol-70 ml ether, the title compound weighs 6.4 g, melting point 215°–217° C.

EXAMPLE 5

2-[1-[4-[3-(Dimethylamino)propoxy]phenyl]ethyl]-3,4-dihydro-6-methoxy-1(2H)-naphthalenone, hydrochloride (1:1)

(A)

2-[[4-[3-(Dimethylamino)propoxy]phenyl]methylene]-3,4-dihydro-6-methoxy-1(2H)-naphthalenone Interaction of 16 g of 6-methoxy-1-tetralone and 19 g of 4-(3-dimethylaminopropoxy)benzaldehyde in 95 ml of ethanol in the presence of 0.6 g of potassium hydroxide following the procedure described in Example 1A, yields 27 g of crude product; melting point 68°–71° C. Following crystallization from 70 ml of diisopropyl ether, the product weighs 18.6 g, melting point 76°–78° C.

(B)
2-[1-[4-[3-(Dimethylamino)propoxy]phenyl]ethyl]-3,4-dihydro-6-methoxy-1(2H)-naphthalenone, hydrochloride (1:1)

2-[[4-[3-(Dimethylamino)propoxy]phenyl]methylene]-3,4-dihydro-6-methoxy-1(2H)-naphthalenone (10 g) is reacted with 15 ml of 3 M methyl magnesium bromide in 90 ml of tetrahydrofuran following the procedure described in Example 1B to give 11.5 g of the free base of the title compound.

The base is dissolved in 60 ml of acetonitrile and treated with a solution of 3.5 g of oxalic acid in 60 ml of acetonitrile to yield 10.5 g of the oxalate salt, melting point 134°–136° C. (sintering at 130° C.). Following crystallization from 200 ml of methanol-300 ml of ether, the oxalate salt weighs 8.1 g, melting point 138°–140° C. (sintering at 132° C.).

The oxalate salt is converted to the base using 4 g of potassium carbonate and ether extractions, and the base (6.0 g) is dissolved in methylene chloride and treated with 3.1 ml of 5.3 N alcoholic hydrogen chloride. After removing the solvents on a rotary evaporator, the glass-like residue is rubbed under ether (evaporation repeated) and stirred with 30 ml of boiling acetone to give (after cooling for about 16 hours), 5.1 g of solid, melting point 111°–114° C. (sintering at 100° C.). This material which forms a solvate with acetone is dissolved in 50 ml of warm chloroform and reprecipitated with 400 ml of ether. The yield of the title compound is 4.6 g, melting point 141°–143° C. (sintering at 130° C.).

EXAMPLE 6

2-[1-[2-[3-(Dimethylamino)propoxy]phenyl]ethyl]-3,4-dihydro-1(2H)-naphthalenone, citrate salt (1:1)

(A)
2-[[2-[3-(Dimethylamino)propoxy]phenyl]methylene]-3,4-dihydro-1(2H)-naphthalenone α-Tetralone (26.4 g) and 40 g of 2-[3-(dimethylamino)propoxy]benzaldehyde are reacted in 180 ml of ethanol in the presence of 1.2 g of potassium hydroxide following the procedure in Example 1A. The product is extracted with ether and the solvent is evaporated to give a viscous residue (67.2 g), which begins to solidify on standing. It is crystallized from a mixture of 120 ml of warm diisopropylether and 120 ml of hexane to give 45.7 g of crystals, melting point 67°–69° C.

(B)
2-[1-[2-[3-(Dimethylamino)propoxy]phenyl]ethyl]-3,4-dihydro-1(2H)-naphthalenone, citrate salt (1:1)

Twenty grams of 2-[[2-[3-(dimethylamino)propoxy]phenyl]methylene]-3,4-dihydro-1(2H)-naphthalenone is reacted with 35 ml of 3 M methyl magnesium bromide in 200 ml of tetrahydrofuran as described in Example 1B. During the addition of the Grignard reagent, a greenish color develops, then changes to yellow and finally to yellow-orange on continued stirring. The product is 23.2 g of the crude free base of the title compound.

The free base (which darkens somewhat on standing) is taken up in 300 ml of methanol, treated with 5.4 g of oxalic acid (color of the solution lightens slightly), and the solvent is removed on a rotary evaporator. The residue is rubbed under ether (two times; evaporation is repeated each time) to give 29 g of a foamy product. When the latter is dissolved in 100 ml of methyl ethyl ketone and kept in the cold for several days, 12.7 g of a hygroscopic solid is obtained, melting point 69°–71° C. (sintering at 59° C.). Trituration first with 60 ml of boiling acetonitrile, then with 20 ml of boiling ethanol, gives 2.2 g of a solid, melting point 162°–164° C. (sintering at 155° C.).

The methyl ethyl ketone, acetonitrile and ethanol filtrates are combined and evaporated to give 21.9 g of a glass-like residue. Since the residue could not be crystallized it was converted to 13.8 g of the oily base (using potassium carbonate and ether extractions).

The above base (12.8 g) and 7.7 g of citric acid monohydrate are dissolved in methanol and the solvent removed on a rotary evaporator to give a gummy residue which is rubbed under ether (three times; evaporation repeated each time, finally at 1 mm of Hg). The resulting solid weighs 20.3 g, melting point 77°–79° C. (foaming; sintering at 50° C.).

Reprecipitation from 60 ml of methanol by adding the solution portionwise to 1 l. of stirred ether yields 19.3 g of the title compound, melting point 77°–79° C. (sintering at 50° C.).

EXAMPLE 7

3,4-Dihydro-2-[1-[4-[3-(4-morpholinyl)propoxy]phenyl]ethyl]1(2H)-naphthalenone, hydrochloride (1:1), hydrate (A)
3,4-Dihydro-2-[4-[3-(4-morpholinyl)propoxy]phenyl]methylene]-1-(2H)-naphthalenone Interaction of 4-[3-(4-morpholinyl)propoxy]benzaldehyde (19 g) and 11.1 g of α-tetralone in 80 ml of ethanol in the presence of 0.5 g of potassium hydroxide following the procedure described in Example 1A gives 21.5 g of product (separates from the reaction mixture), melting point 112°–114° C. (sintering at 100° C.). Workup of the filtrate yields an additional 7.6 g of crude material. The two fractions are combined and crystallized from 150 ml of acetonitrile to give 23.3 g of product, melting point 115°–117° C. (sintering at 111° C.).

(B)
3,4-Dihydro-2-[1-[4-[3-(4-morpholinyl)propoxy]phenyl]ethyl]-1(2H)-naphthalenone, hydrochloride, (1:1), hydrate 3,4-Dihydro-2-[4-[3-(4-morpholinyl)propoxy]phenyl]methylene]-1(2H)-naphthalenone (12 g) is reacted with 18 ml of 3 M methyl magnesium bromide in 120 ml of tetrahydrofuran according to the procedure described in Example 1B to give 14.7 g of crude oily base. The base is dissolved in dichloromethane, treated with 5.8 ml of 5.5 N alcoholic hydrogen chloride, and the solvents evaporated to give a gummy residue which is converted to a brittle solid by rubbing under ether and repeating the evaporation. Trituration with 100 ml of boiling acetone, followed by overnight cooling, yield 6.3 g of solid, melting point 143°–145° C. (sintering at 100° C.). The filtrate is evaporated and the glass-like residue triturated with 30 ml of boiling acetone and cooled to give 1.5 g of a second crop. Following crystallization of the combined crops from 30 ml methanol-60 ml ether, the title compound weighs 5.6 g, melting point 145°–147° C. (sintering at 105° C.).

EXAMPLE 8

2-[[4-[3-(Dimethylamino)propoxy]phenyl]phenylmethyl]-2,3-dihydro-1H-inden-1-one, hydrochloride (1:1)

(A)

2-[[4-[3-(Dimethylamino)propoxy]phenyl]methylene]-2,3-dihydro-1H-inden-1-one

Interaction of 56 g of 1-indanone and 88 g of 4-(3-dimethylaminopropoxy)benzaldehyde according to the procedure described in Example 1A, gives 134.2 g of an oily product.

(B)

2-[[4-[3-(Dimethylamino)propoxy]phenyl]phenylmethyl]-2,3-dihydro-1H-inden-1-one, hydrochloride (1:1)

Interaction of 29 g of 2-[[4-[3-(dimethylamino)propoxy]phenyl]methylene]-2,3-dihydro-1H-inden-1-one in 300 ml of tetrahydrofuran with 50 ml of 3.2 N phenyl magnesium bromide in ether according to the procedure described in Example 3 gives 10.4 g of an oily product. This material, when treated with hydrogen chloride, yields the title compound, melting point 182°–184° C. (after recrystallization from methanolether).

EXAMPLES 9–25

Following the procedure of Example 1, but substituting the compound listed in column I for α-tetralone, the compound listed in column II for 4-(3-dimethylaminopropoxy)benzaldehyde, and the compound listed in column III for methyl magnesium bromide, yields the oxalate salt of the compound listed in column IV.

| Column I | Column II | Column III | Column IV |
|---|---|---|---|
| 7-chloro-α-tetralone | 4-[2-(1-piperidinyl)ethoxy]benzaldehyde | 4-chlorophenyl magnesium bromide | 7-chloro-3,4-dihydro-2-[[4-[2-(1-piperidinyl)ethoxy]phenyl](4-chlorophenyl)methyl]-1(2H)-naphthalenone |
| 6-methyl-α-tetralone | 2-[4-(1-pyrrolidinyl)butoxy]benzaldehyde | 4-methylphenyl magnesium bromide | 3,4-dihydro-6-methyl-2-[[2-[4-(1-pyrrolidinyl)butoxy]phenyl](4-methylphenyl)methyl]-1(2H)-naphthalenone |
| 6-methoxy-α-tetralone | 3-[3-(4-methyl-1-piperidinyl)propoxy]benzaldehyde | 4-methoxyphenyl magnesium bromide | 3,4-dihydro-6-methoxy-2-[[3-[3-(4-methyl-1-piperidinyl)propoxy]phenyl](4-methoxyphenyl)methyl]-1(2H)-naphthalenone |
| 7-trifluoromethyl-α-tetralone | 4-[5-[4-(2-hydroxyethyl)-1-piperidinyl]pentoxy]benzaldehyde | 3-(trifluoromethyl)phenyl magnesium bromide | 3,4-dihydro-2-[[4-[5-[4-(2-hydroxyethyl)-1-piperidinyl]pentoxy]phenyl][3-(trifluoromethyl)phenyl]methyl]-7-trifluoromethyl-1(2H)-naphthalenone |
| 5-fluoro-1-indanone | 4-(2-methylaminoethoxy)benzaldehyde | methyl magnesium bromide | 5-fluoro-2,3-dihydro-2-[1-[4-[2-(methylamino)ethoxy]phenyl]ethyl]-1H-inden-1-one |
| 5-ethyl-1-indanone | 3-[3-(1-piperidinyl)propoxy]benzaldehyde | phenyl magnesium bromide | 5-ethyl-2,3-dihydro-2-[[3-[3-(1-piperidinyl)propoxy]phenyl]phenylmethyl]-1H-inden-1-one |
| 6-ethoxy-1-indanone | 4-[2-(1-pyrrolidinyl)ethoxy]benzaldehyde | 4-iodophenyl magnesium bromide | 6-ethoxy-2,3-dihydro-2-[[4-[2-(1-pyrrolidinyl)ethoxy]phenyl](4-iodophenyl)methyl]-1H-inden-1-one |
| 6-trifluoromethyl-1-indanone | 2-[4-(4-morpholinyl)butoxy]benzaldehyde | 2-ethylphenyl magnesium bromide | 2,3-dihydro-2-[[2-[4-(4-morpholinyl)butoxy]phenyl](2-ethylphenyl)methyl]-6-trifluoromethyl-1H-inden-1-one |
| 6-bromo-1-indanone | 4-[5-(4-methyl-1-piperidinyl)pentoxy]benzaldehyde | 2-ethoxyphenyl magnesium bromide | 6-bromo-2,3-dihydro-2-[[4-[5-(4-methyl-1-piperidinyl)pentoxy]phenyl](2-ethoxyphenyl)methyl]-1H-inden-1-one |
| 5-isopropyl-1-indanone | 4-[2-[4-(2-hydroxyethyl)-1-piperidinyl]ethoxy]benzaldehyde | phenyl magnesium bromide | 2,3-dihydro-2-[[4-[2-[4-(2-hydroxyethyl)-1-piperidinyl]ethoxy]phenyl]phenylmethyl]-5-isopropyl-1H-inden-1-one |
| 1-benzosuberone | 4-(3-diethylaminopropoxy)benzaldehyde | phenyl magnesium bromide | 6-[[4-[3-(diethylamino)propoxy]phenyl]phenylmethyl]-6,7,8,9-tetrahydro-5H-benzocyclohepten-5-one |
| 2-iodo-1-benzosuberone | 2-(2-ethylaminoethoxy)benzaldehyde | 3-(trifluoromethyl)phenyl magnesium bromide | 6-[[2-[2-(ethylamino)ethoxy]phenyl][3-(trifluoromethyl)phenyl]methyl]-2-iodo-6,7,8,9-tetrahydro-5H-benzocyclohepten-5-one |
| 3-methyl-1-benzosuberone | 4-[2-(1-piperidinyl)ethoxy]benzaldehyde | 4-chlorophenyl magnesium bromide | 3-methyl-6-[[4-[2-(1-piperidinyl)ethoxy]phenyl](4-chlorophenyl)methyl]-6,7,8,9-tetrahydro-5H-benzocyclohepten-5-one |
| 2-methoxy-1-benzo- | 3-[3-(1-pyrrolidinyl)- | 4-methoxyphenyl | 2-methoxy-6-[[3-[3-(1- |

-continued

| Column I | Column II | Column III | Column IV |
| --- | --- | --- | --- |
| suberone | propoxy]benzaldehyde | magnesium bromide | pyrrolidinyl)propoxy]phenyl](4-methoxyphenyl)methyl]-6,7,8,9-tetrahydro-5H-benzocyclohepten-5-one |
| 3-fluoro-1-benzosuberone | 4-[4-(4-morpholinyl)butoxy]benzaldehyde | 4-fluorophenyl magnesium bromide | 3-fluoro-6-[[4-[4-(4-morpholinyl)butoxy]phenyl](4-fluorophenyl)methyl]-6,7,8,9-tetrahydro-5H-benzocyclohepten-5-one |
| 3-trifluoromethyl-1-benzosuberone | 3-[2-(4-methyl-1-piperidinyl)ethoxy]benzaldehyde | phenyl magnesium bromide | 6-[[3-[2-(4-methyl-1-piperidinyl)ethoxy]phenyl]phenylmethyl]-3-trifluoromethyl-6,7,8,9-tetrahydro-5H-benzocyclohepten-5-one |
| 1-benzosuberone | 4-[5-[4-(2-hydroxyethyl)-1-piperidinyl]pentoxy]benzaldehyde | phenyl magnesium bromide | 6-[[4-[5-[4-(2-hydroxyethyl)-1-piperidinyl]pentoxy]phenyl]phenylmethyl]-6,7,8,9-tetrahydro-5H-benzocyclohepten-5-one |

What is claimed is:

1. A compound having the formula

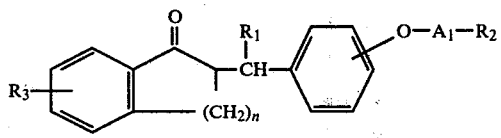

or a pharmaceutically acceptable salt thereof, wherein $R_1$ is hydrogen, alkyl, phenyl or phenyl substituted with a halogen, alkyl, alkoxy or trifluoromethyl group; $R_2$ is alkylamino, dialkylamino, 1-piperidinyl, 1-pyrrolidinyl, 4-morpholinyl, 4-alkyl-1-piperidinyl or 4-(2-hydroxyethyl)-1-piperidinyl; $R_3$ is hydrogen, halogen, alkyl, alkoxy, or trifluoromethyl; $A_1$ is a straight or a branched chain alkylene group having 2 to 5 carbon atoms; and n is 1, 2 or 3; wherein the terms "alkyl" and "alkoxy" refer to groups having 1 to 8 carbon atoms.

2. A compound in accordance with claim 1 wherein $R_1$ is hydrogen.

3. A compound in accordance with claim 1 wherein $R_1$ is alkyl, phenyl, or phenyl substituted with a halogen, alkyl, alkoxy or trifluoromethyl group.

4. A compound in accordance with claim 3 wherein $R_1$ is alkyl.

5. A compound in accordance with claim 3 wherein $R_1$ is phenyl or phenyl substituted with a halogen, alkyl, alkoxy or trifluoromethyl group.

6. A compound in accordance with claim 1 wherein n is 1.

7. A compound in accordance with claim 1 wherein n is 2.

8. A compound in accordance with claim 1 wherein n is 3.

9. A compound in accordance with claim 1 wherein $R_2$ is alkylamino or dialkylamino.

10. A compound in accordance with claim 9 wherein $R_2$ is dialkylamino.

11. The compound in accordance with claim 1 having the name 2-[1-[4-[3-(dimethylamino)propoxy]phenyl]ethyl]-3,4-dihydro-1(2H)-naphthalenone, oxalate salt (1:1).

12. The compound in accordance with claim 1 having the name 2-[1-[4-[3-(dimethylamino)propoxy]phenyl]pentyl]-3,4-dihydro-1(2H)-naphthalenone, oxalate salt (1:1).

13. The compound in accordance with claim 1 having the name 2-[[4-[3-(dimethylamino)propoxy]phenyl]phenylmethyl]-3,4-dihydro-1(2H)-naphthalenone, hydrochloride (1:1).

14. The compound in accordance with claim 1 having the name 2-[[4-[3-(dimethylamino)propoxy]phenyl]methyl]-3,4-dihydro-1(2H)-naphthalenone, hydrochloride (1:1).

15. The compound in accordance with claim 1 having the name 2-[1-[4-[3-(dimethylamino)propoxy]phenyl]ethyl]-3,4-dihydro-6-methoxy-1(2H)-naphthalenone, hydrochloride (1:1).

16. The compound in accordance with claim 1 having the name 2-[1-[2-[3-(dimethylamino)propoxy]phenyl]ethyl]-3,4-dihydro-1(2H)-naphthalenone, citrate salt (1:1).

17. The compound in accordance with claim 1 having the name 3,4-dihydro-2-[1-[4-[3-(4-morpholinyl)propoxy]phenyl]ethyl]-1(2H)-naphthalenone, hydrochloride (1:1), hydrate.

18. The compound in accordance with claim 1 having the name 2-[[4-[3-(dimethylamino)propoxy]phenyl]phenylmethyl]-2,3-dihydro-1H-inden-1-one, hydrochloride (1:1).

* * * * *